United States Patent [19]

Grimminger et al.

[11] Patent Number: 4,855,422

[45] Date of Patent: Aug. 8, 1989

[54] PROCESSES FOR THE PREPARATION OF AZONIASPIRONORTROPANOL ESTERS

[75] Inventors: Wolf Grimminger; Klaus Görler, both of Gladbach; Karl P. Odenthal, Grevenbroich, all of Fed. Rep. of Germany

[73] Assignee: Madaus GmbH & Co., Köln, Fed. Rep. of Germany

[21] Appl. No.: 945,488

[22] Filed: Dec. 23, 1986

[30] Foreign Application Priority Data

Dec. 27, 1985 [DE] Fed. Rep. of Germany ....... 3546218

[51] Int. Cl.$^4$ ................. C07D 401/00; C07D 237/00; C07D 265/00; C07D 239/00
[52] U.S. Cl. ..................................... 540/466; 546/18; 540/543; 544/231; 544/71; 544/230
[58] Field of Search ................... 546/18; 544/126, 127, 544/342, 343, 231, 71, 230; 514/227, 280, 281, 282, 250, 289; 540/543, 466

[56] References Cited

FOREIGN PATENT DOCUMENTS 1194422 5/1963 Fed. Rep. of Germany ........ 546/18
2003680 1/1970 Fed. Rep. of Germany ........ 546/18

OTHER PUBLICATIONS

Bertholdt et al(I), CA, vol. 68, 1968, 68:12841s.
Bertholdt et al.(II), CA, vol 68, 1968, 68:12840r.
Pfister, CA, vol. 94, 1981, 94:47156m.
Markushma et al, CA, vol. 84, 84:17175t.
Bertholdt et al(III), CA, vol. 70, 1969 70:68284w.
Ito et al(I), CA, vol. 76, 1972, 76:149165j.
Ito et al.(II), CA, vol. 81, 1974, 81:114745z.
Findlay, JACS vol. 75: pp. 3204–3208 (1953).
Kim, Org. Prep & Proc. Int. 9(1): pp. 1–4 (1977).
Kraiss, et al., Tet. Lett. 1: pp. 57–58 (1971).
Berthold, et al., Arzneim Forsch 17(6): pp. 714–719 (1967).
Montzka, et al., Tet. Lett. 14: pp. 1325–1327 (1974).
Staab, et al., Chem. Ber. 95: pp. 1284–1297 (1962).

Primary Examiner—Mary C. Lee
Assistant Examiner—Robert C. Whittenbaugh
Attorney, Agent, or Firm—Felfe & Lynch

[57] ABSTRACT

A method for preparing azoniaspironotropanol esters, esters thus produced, and methods of use for these is disclosed. The esters are effective as broncholytics and as agents in therapy of asthmatic conditions.

16 Claims, No Drawings

PROCESSES FOR THE PREPARATION OF AZONIASPIRONORTROPANOL ESTERS

The present invention is concerned with a process for the preparation of azoniaspironortropanol esters, as well as new azoniaspironortropanol esters and pharmaceutical compositions which contain these compounds.

Because of their excellent spasmolytic properties, azoniaspironortropane derivatives are frequently used pharmaceutically. These compounds are prepared from the naturally occurring tropine but the known processes are laborious and time-consuming and, because of the low yields obtained, are also expensive.

Usually, the preparation of azoniaspironortropane derivatives takes place according to the following reaction scheme:

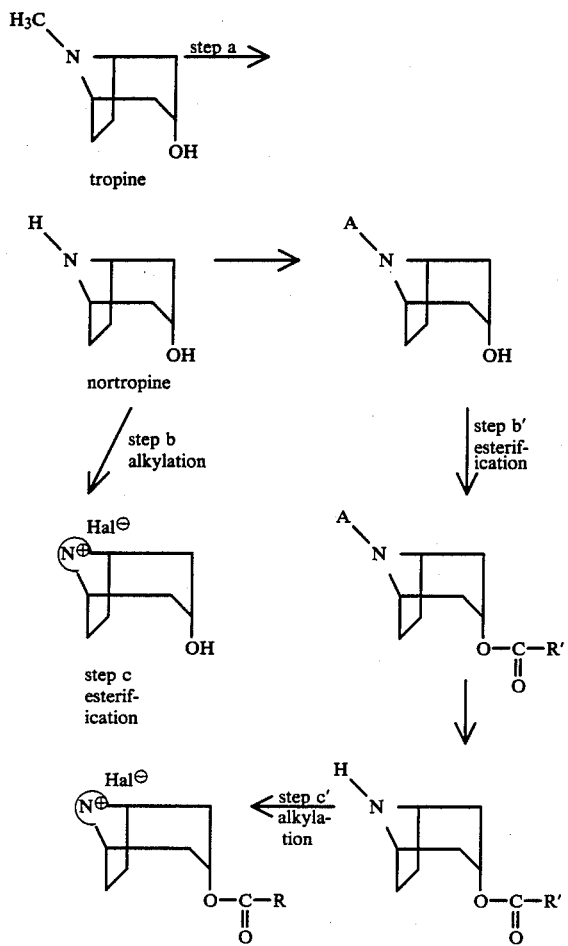

In the above scheme, R' signifies the residue of a carboxylic acid and A is an amino protective group.

The oxidative demethylation of tropine to give nortropine (step a) is described by S. P. Findley in J.A.C.S., 75, 3204/1953. However, this process, which takes place with a supersaturated tropine solution at 15° C. and with a reaction time of from 4 to 7 days, cannot be carried out on a technical scale since, under these reaction conditions, the tropine concentration needed for the reaction cannot be kept stable because the tropine precipitates out spontaneously and is thus removed from the further reaction. A homogenisation of the precipitated tropine, for example by an in-line homogeniser, also did not produce any noticeable improvement.

It is also known to carry out the demethylation by exchange of the methyl radical for an N-alkoxycarbonyl radical and subsequent hydrolysis of the alkoxycarbamate (see J. C. Kirn, Org. Prep. Proc. Int., 9, 1–4/1977). In the case of 8-ethoxycarbonylnortropine, the best yield of nortropine to be found in the literature is 16%, referred to tropine (see G. Kraiss and K. Nador, Tetrahedron Letters, 1971, pp. 7–8). Later, it was even reported that an acidic or alkaline splitting of 8-ethoxycarbonylnortropine is not possible (see T. A. Monzka, J. D. Matiskella and R. A. Partyka, Tetrahedron Letters, 1974, pp. 1325–1327).

The preparation of azoniaspironortropane derivatives by quaternisation and esterification or by the reverse reaction sequence is known from Federal Republic of Germany Patent Specification No. 1,194,422 and from Arzneimittelforschung, 17, 714–719/1967 (steps b and c or steps b' and c'). The hydroxyl group of the nortropine or of the corresponding azoniaspiro compound is thereby esterified by reaction with the appropriate acid chlorides, the hydroxyl group of hydroxycarboxylic acids and possibly the NH group of the nortropine thereby having to be protected. A disadvantage of the processes described in these publications is the poor yield, the esterification of the nortropine (step b') and the subsequent reaction with a dihalide (step c') thereby also requiring two further reaction steps. It has long been known to use acid imidazolides as reagents for the esterification of alcohols (see Chem. Ber., 95, 1284–1297/1962). In particular, Federal Republic of Germany Patent Specification No. 2,003,680 describes the reaction of benzilic acid imidazolide with alcohols of thioalcohols which contain a tertiary amino group.

It is an object of the present invention to provide a process for the preparation of azoniaspironortropanol esters which can be carried out on a technical scale and which permits these compounds to be prepared in a simple manner in good yield.

Surprisingly, we have now found that azoniaspironortropanol esters can be prepared in good yield when the demethylation of tropine is carried out in the presence of a $C_1$–$C_3$-chloroalkane which contains a trichloromethyl radical. The nortropine thus obtained is alkylated with a dihalide in the presence of an amine and the corresponding azoniaspiro compound is esterified by reaction with an acid imidazolide in the presence of a catalyst.

Thus, according to the present invention, there is provided a process for the preparation of azoniaspironortropanol esters of the general formula:

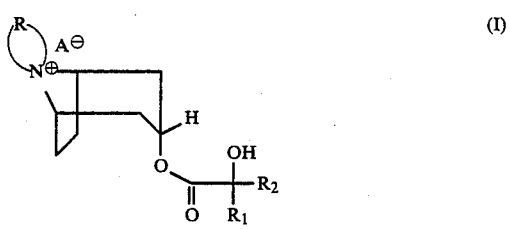

wherein R signifies one of the following radicals:
(a) an alkylene radical of the general formula:

$$-(CH_2)_n-\underset{\underset{R_3}{|}}{CH}-(CH_2)_n-$$

in which $R_3$ is a hydrogen atom or an alkyl, benzyl, aryl or alkoxy radical and n is a whole number of from 1 to 4, (b) an alkenylene radical of the general formula:

$$\underset{(CH_2)_n}{R_4}C=C\underset{(CH_2)_n}{R_5}$$

in which $R_4$ and $R_5$, which can be the same or different, are hydrogen atoms or alkyl or alkenyl radicals and n is a whole number of from 1 to 4;

(c) an azaalkylene radical of the general formula:

$$-(CH_2)_n-\underset{\underset{R_6}{|}}{N}-(CH_2)_n-$$

in which $R_6$ is a hydrogen atom or an alkyl, alkoxycarbonyl or acyl radical and n is a whole number of from 2 to 4;

(d) an oxaalkylene radical of the general formula:

$$-(CH_2)_n-O-(CH_2)_n-$$

in which n is a whole number of from 2 to 4;

(e) an epoxyalkylene radical of the formula:

$$-CH_2-CH\underset{O}{\overset{}{-}}CH-CH_2-$$

(f) an o-phenylene radical of the general formula:

[structure with X, Y on benzene ring and $-H_2C$, $CH_2-$ substituents]

(g) a peri-naphthylene radical of the general formula:

[naphthalene structure with X, Y and $-H_2C$, $CH_2-$ substituents]

(h) a 2,3-quinoxalinene radical of the general formula:

[quinoxaline structure with X, Y and $-H_2C$, $CH_2-$ substituents]

in which, in formulae (f) to (h), the symbols X and Y, which can be the same or different, are hydrogen atoms or alkyl or alkoxy radicals;

and wherein $R_1$ and $R_2$, which can be the same or different, are hydrogen or halogen atoms or alkyl, alkoxy, alkoyl, cyclohexyl, phenyl, alkylphenyl, alkoxyphenyl, halophenyl, thienyl or furyl radicals, the alkyl moieties in the said radicals containing up to 6 carbon atoms and being straight-chained or branched, and $A^{\ominus}$ is the anion of a mono- to tribasic mineral acid, by (a) demethylation of tropine to give nortropine, (b) reaction of nortropine with a dihalide to give the corresponding azonia compound and (c) esterification of the azonia compound, wherein (A) the demethylation of tropine of the formula:

[tropine structure with $H_3C-N$ and OH] (II)

is carried out either by working in a $C_1-C_3$-chloroalkane which contains at least one trichloromethyl radical in the presence of an oxidation agent in basic aqueous solution or the tropine is reacted with a chloroformic acid ester in an inert solvent in the presence of an acid-binding agent to give an 8-alkoxycarbonylnortropine and this is hydrolysed with a base in aqueous solution, (B) the nortropine thus obtained of the formula:

[nortropine structure with H-N and OH] (III)

is reacted at ambient temperature for 1 or more days in a dipolar aprotic solvent with a compound of the general formula:

$$A-R-A$$

in which A and R have the above-given meanings, in the presence of a secondary or tertiary amine and (C) the compound thus obtained of the general formula:

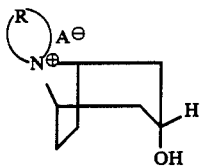

(IV)

in which R and A⊖ have the above-given meanings, is esterified in an anhydrous, dipolar, aprotic solvent with an imidazolide of the general formula:

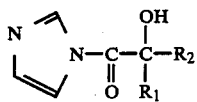

(V)

in which $R_1$ and $R_2$ have the above-given meanings, in the presence of a catalyst.

In the above-defined radicals, n can be the same or different, the radicals n preferably being so selected that there is a 5- or 6-membered ring.

The anion A⊖ is preferably a halide ion, such as a chloride, bromide or iodide ion, or a phosphate, sulphate or nitrate ion.

Preferred examples of the radical R include the following:

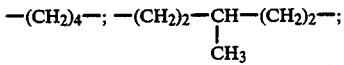

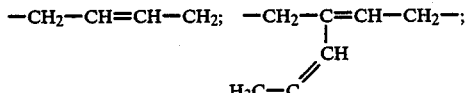

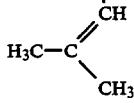

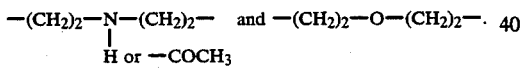

Within the scope of the present invention, the alkyl radicals, including those present in alkoxy, acyl, alkylamino and the like radicals, can be straight-chained or branched and contain up to 18 carbon atoms and preferably up to 6 and more preferably up to 4 carbon atoms. Specific examples of such radicals include methyl, ethyl, n-propyl, isopropyl, n-butyl, hexyl, lauryl and stearyl radicals.

Preferred acyl radicals include the acetyl and benzoyl radicals.

(D) When the radical R contains one or more olefinic double bonds in the azonium ring after passing through steps B and/or C, these unsaturated compounds can be hydrogenated in a polar solvent with the help of a noble metal catalyst to give the corresponding saturated compounds, compounds of general formula (I) then being obtained in which R is a radical (a) as defined above.

Step A

This process step makes possible the demethylation even on a technical scale and gives nortropine in considerably higher yields in comparison with the prior art. Two process variants can thereby be used, namely, oxidative demethylation or the carbamate method.

The advantages of the oxidative method depend upon the use of a $C_1$–$C_3$-chloroalkane containing at least one trichloromethyl radical which is finely dispersed in the aqueous phase. Examples of chloroalkanes which can be used include, for example, 1,1,1-trichloroethane, 1,1,1-trichloropropane and preferably chloroform. The amount of chloroalkane used is in the range of from 1–10% by volume, preferably from 1 to 5% by volume and most preferably from 2 to 4% by volume.

For the demethylation, there can be employed any oxidation agent normally used for this purpose, potassium ferricyanide being preferred.

The process can be carried out in a wide temperature range, for example of from 0° to 100° C. but it is preferred to work at a temperature of from 20° to 30° C. When the reaction is finished, the product is extracted in counter-current, preferably with the solvent used for the demethylation.

The oxidative method results in a considerable saving of time in comparison with the known methods, which additionally improves the economy of the process according to the present invention.

However, it is preferred to use the carbamate method. For this purpose, tropine is reacted in an inert solvent with a 4 to 6 fold excess of a chloroformic acid ester and generally with ethyl chloroformate. As solvent, there is thereby preferably used a chlorinated hydrocarbon, especially chloroform. The reaction is carried out in the presence of an acid-binding agent, preferably of an alkali metal carbonate or bicarbonate. Working is carried out at an elevated temperature, preferably in the range of from 40° to 80° C.

After substantial distilling off of the solvent, the 8-alkoxycarbonylnortropine thus obtained is hydrolysed with a base in aqueous solution. As base, there is preferably used potassium or sodium hydroxide, preferably in 16 to 20 fold excess.

The nortropine is extracted from the aqueous reaction mixture in the manner described above for the oxidation demethylation.

According to step A, nortropine can be obtained in almost quantitative yield, especially according to the carbamate method.

Step B

The crude nortropine obtained in step A can be used in step B without further purification, in contradistinction to the prior art which requires 48 hours of continuous extraction and crystallisation from diethyl ether. We have, surprisingly, found that the tropine still present in the crude nortropine as impurity is not quaternised under the reaction conditions of step B.

Solvents which can be used for quaternising the nortropine include, for example, N,N-dimethylformamide, chloroform or chloroform/acetonitrile. With dihalides in the presence of secondary or tertiary amines, after a reaction period of one or more days at ambient temperature, the corresponding azoniaspiro compounds are obtained in pure form and with high yields. It is preferred to work in anhydrous solution, using nortropine, amine and dihalide in a mole ratio of 1:2:4. As already mentioned, the product obtained in good yield is of high purity so that a further purification is not necessary.

Secondary amines which can be used for this reaction include, for example, dimethylamine, diethylamine, diisopropylamine, dicyclohexylamine and the like. Examples of tertiary amines which can be used include trimethylamine, triethylamine, pyridine, quinoline and the like. The use of diethylamine is preferred.

Step C

Not only the azoniaspiro compounds obtained from step B but also the carboxylic acid imidazolides are generally of low solubility in the anhydrous, dipolar, aprotic solvents usually employed for such a reaction, for example acetone, acetonitrile, dimethylformamide, tetrahydrofuran and the like. If it is endeavoured to overcome the problems therewith involved by increasing the reaction temperature, then the products resulting therefrom are contaminated with a high proportion of by-products. In particular, carboxylic acid imidazolides which have an unprotected hydroxyl group react with themselves at an elevated temperature.

Surprisingly, we have now found that the reaction of a compound of general formula (IV) with a carboxylic acid imidazolide of general formula (V) can be carried out in the presence of an appropriate catalyst even in the above-mentioned anhydrous, dipolar, aprotic solvents by reacting the reaction components in suspension. The advantage of this process is that the free hydroxyl groups of the carboxylic acid imidazolides do not have to be protected and that the reaction product precipitates from the above-mentioned solvents and, therefore, can be isolated in a simple manner. The reaction product is not, as was to have been expected, contaminated by a reactant introduced into the reaction in solid form. Furthermore, the reaction takes place under such mild conditions that no fragmentation and elimination reactions attributable to the presence of the quaternary ammonium group take place. Consequently, no corresponding by-products can be formed.

4-(Dimethylamino)-pyridine has proved to be the most advantageous catalyst for this process. This compound can be used in amounts of from 1 to 30 mole % and preferably of from 5 to 10 mole %, referred to the benzilic acid imidazolide.

As solvents, there can be used the above-mentioned anhydrous, dipolar, aprotic solvents. The reaction is carried out at an elevated temperature and preferably at a temperature of from 60° to 80° C.

The preparation of the carboxylic acid imidazolides used in this reaction takes place in known manner by reacting N,N-carbonyldiimidazole with the appropriate carboxylic acids in dry dichloromethane.

Step D

Since, in the case of the quaternisation according to step (B) with the dihalides substituted on the double bond, for example with cis-1,4-dichlorobutene, a much greater speed of reaction is achieved, for example from 18 days to 1 hour, it can be advantageous for the preparation of compounds of general formula (I), in which R has the meaning of a radical such as (a), for example a benziloyloxynortropane-8-spiro-1'-pyrrolidinium salt, to choose the route via the corresponding unsaturated compounds with subsequent catalytic hydrogenation either after passing through step (B) or steps (B) and (C).

The hydrogenation of the unsaturated compounds is carried out in a polar solvent, such as water or an alcohol containing up to 4 carbon atoms, preferably methanol, in the presence of a noble metal catalyst, such as platinium dioxide or palladium on active charcoal.

In the case of using an unsaturated halide, in carrying out the quaternisation there is used a considerably smaller excess of dihalide. The mole ratio of nortropine, amine and dihalide previously stated to be preferably 1:2:4 in step (B) can then be changed to 1:2:2.

The present invention also provides new azoniaspironortropanol esters of the general formula:

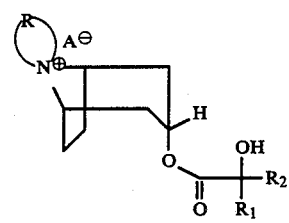

wherein R, $R_1$, $R_2$ and $A^\ominus$ have the same meanings as in claim 1, but excluding the following compounds:
azoniaspiro-[3α-phenylglycoloyloxynortropan-8,1'-pyrrolidine]chloride,
azoniaspiro-[3α-diphenylglycoloyloxynortropan-8,1'-pyrrolidine]chloride,
3α-phenylglycoloyloxynortropan-8-spiroisoindolinium chloride,
3α-diphenylglycoloyloxynortropan-8-spiroisoindolinium chloride,
3α-phenylglycoloyloxynortropan-8-spiro-4'-morpholinium chloride,
3α-diphenylglycoloyloxynortropan-8-spiro-4'-morpholinium chloride,
azoniaspiro-[3α-cyclohexylphenylglycoloylnortropan-8,1'-pyrrolidine]chloride,
azoniaspiro-[3α-phenylglycoloyloxynortropan-8,1'-piperidine]chloride and
azoniaspiro-[3α-diphenylglycoloyloxynortropan-8,1'-piperidine]chloride.

These compounds possess outstanding spasmolytic properties.

In addition, the present invention provides pharmaceutical compositions containing at least one of the compounds according to the present invention, optionally in admixture with pharmaceutically-acceptable carriers and/or adjuvants.

The following Examples are given for the purpose of illustrating the present invention:

EXAMPLE 1

3α-Benziloyloxynortropane-8-spiro-1'-pyrrolidinium chloride

Step A

Demethylation of tropine to nortropine

In a 300 liter stirrer vessel equipped with a reflux condenser, 1.9 kg. tropine (97%, corresponding to 1.843 kg. of pure compound, equal to 13 mole) are dissolved in 240 liters chloroform and 5.7 kg. sodium hydrogen carbonate powder and 5.3 liters ethyl chloroformate (98%, corresponding to 6.0 kg. and to 55.7 mole) are stirred in. The reaction mixture is heated to the boil and then heated under reflux for a further 2 hours. The progress of the reaction is monitored by means of thin layer chromatography (silica gel 60; dimethylformamide/diethylamine/ethanol/ethyl acetate 5:10:30:60 v/v/v/v). The reaction mixture is filtered while hot and the chloroform is distilled off. A solution of 18 kg. 85% potassium hydroxide in 90 liters water is added to the residue. The reaction mixture is heated to the boil and then heated under reflux for a further 9 hours. The cooled solution is then extracted with chloroform using a Karr column. Extraction conditions: the "stationary" phase is the light phase (aqueous potassium hydroxide solution) which is conveyed at a rate of about 14 liters/hour. The dispersed phase is the heavy chloroform phase which is conveyed at a rate of about 35 to 50 liters/hour. Shaking frequency: 200 strokes/minute; temperature 26° to 28° C.

In this way, the nortropine formed is extracted from the aqueous potassium hydroxide solution in almost quantitative yield. After stripping off the solvent, the crude product obtained is used in the following step (B) without further purification. There is obtained 1.876 kg. nortropine with a content of 87% (high pressure liquid chromatography: $\mu$-Bondapack $C_{18}$-column; elution agent: methanol/water 1:9 v/v with PIC-B7). This corresponds to 1.632 kg. of pure tropine and to a yield of 98%.

Step B

3$\alpha$-Hydroxynortropane-8-spiro-1'-pyrrolidinium chloride

The composition of the reaction mixture must be referred to pure nortropine and the mole ratio of nortropine:diethylamine:1,4-dichlorobutane must be exactly 1:2:4.

The crude nortropine obtained in step (A) (1.186 kg., corresponding to 1.632 kg. of pure substance and to 12.85 mole) is dissolved in 52 liters N,N-dimethylformamide and 2.665 liters (1.876 kg.; 25.7 mole) diethylamine and 5.736 liters (6.528 kg.; 5.14 mole) 1,4-dichlorobutane added thereto. The reaction mixture is left to stand for 18 days at ambient temperature. The crystals which separate out are filtered off with suction, washed with a little dry acetonitrile and dried at 50° C. in a vacuum drying cabinet. There are obtained 2.25 kg. (80%, referred to the amount of tropine used in the first step) of pure product; m.p. 250° C.

Step C

3$\alpha$-Benziloyloxynortropane-8-spiro-1'-pyrrolidinium chloride (trospium chloride)

(a) Benzilic acid imidazolide 1.944 kg. (12 mole) N,N-carbonyldiimidazole are dissolved in 19.2 liters dry dichloromethane with the exclusion of moisture. 2.736 kg. (12 mole) dry benzilic acid are added thereto, while stirring, at 15° to 20° C. in the course of 6 minutes, whereafter the reaction mixture is stirred for 1 hour at ambient temperature. The benzilic acid thereby first goes into solution but soon afterwards the benzilic acid imidazolide begins to separate out in solid form. It is filtered off with suction and washed with 0.8 liters dry dichloromethane. There are obtained 2.4 kg. benzilic acid imidazolide.

(b) Preparation of the title compound

In a 300 liter stirrer vessel, 1.3 kg. of the compound obtained in step (B) are suspended in 230 liters anhydrous acetonitrile and heated to 78° C. A solution of 74.0 g. 4-(dimethylamino)-pyridine in 2 liters anhydrous acetonitrile is added thereto. A suspension of 2.086 kg. benzilic acid imidazolide in 9.0 liters anhydrous acetonitrile is then added thereto in three portions at intervals of 30 minutes at 78° C. The reaction mixture is subsequently stirred at 78° C. until there is achieved a total reaction time of 4 hours after the first addition of benzilic acid imidazolide. The reaction mixture is then cooled to 20° C. and further stirred overnight. The suspension formed is filtered off with suction and washed with some acetonitrile. The residue, as well as further product obtained by concentration of the mother liquor (total 2.14 kg.), are recrystallised from isopropanol. There is obtained 1.78 kg. (70%) of pure product; m.p. 258°-263° C. (decomp.).

FD-MS: m/e=392 (molecule cation).
IR (KBr): $\gamma$=3150, 1735, 1498, 1452, 747.

EXAMPLE 2

3$\alpha$-Benziloyloxynortropane-8-spiro-1'-(3'-pyrrolidinium)

Step B

3$\alpha$-Hydroxynortropane-8-spiro-1'-(3'-pyrrolidinium) chloride 1.05 ml. (10 mMole) diethylamine and 1.05 ml. (10 mMole) cis-1,4-dichlorobut-2-ene are stirred into a solution of 635 mg. (5 mMole) nortropine in 9.5 ml. N,N-dimethylformamide. After 1 hour, the pure crystalline product is filtered off with suction. The mother liquor is mixed with ethyl acetate until the commencement of turbidity in order to obtain further product. The crystals are filtered off with suction and washed with a little acetone. Yield 984 mg. (91% of theory); m.p. 204° C.

FD-MS: m/e=180 (molecule cation).
IR (KBr): $\gamma$=3250, 1621 cm$^{-1}$.
$^1$H-NMR (90 MHz, D$_2$O, $\delta$-values referred to TSP=0): $\delta$=1.7-2.7 (8H; H-2, H-4, H-6, H-7); 3.92 (2H; H-1, H-5); 4.05 (1H; H-3); 4.14 and 4.31 (each 2H; H-2' and H-5'); 5.90 (2H; J-3', H-4').

Step C

3$\alpha$-Benziloyloxynortropane-8-spiro-1'-(3'-pyrrolinium) chloride 530 mg. (2.4 mMole) 3$\alpha$-hydroxynortropane-8-spiro-1'-(3'-pyrrolinium) chloride are suspended in 353 ml. anhydrous acetone and stirred in an autoclave for 23 hours at 70° C. with 14 mg. (0.12 mMole) 4-dimethylaminopyridine and 678 mg. (2.4 mMole) benzilic acid imidazolide. Upon cooling to ambient temperature, the product crystallises out of the reaction mixture. It is filtered off with suction and washed with a little acetone. Yield 650 mg. (62% of theory); m.p. 267° C.

FD-MS: m/e=390 (molecule cation).
IR (KBr): $\gamma$=1722, 1595, 1490, 1445, 741 cm$^{-1}$.
$^1$H-NMR (90 MHz, D$_2$O, $\delta$-values referred to TSP=0): $\delta$=1.3-2.8 (8H; H-2, H-4, H-6, H-7); 3.85 (2H; H-1, H-5); 4.09 and 4.37 (each 2H; H-2' and H-5'); 5.24 (1H; H-3); 5.95 (2H; H-3'); 7.44 (10H; aromatic protons of the benzilic acid).

Step D

Conversion of 3$\alpha$-benziloyloxynortropane-8-spiro-1'-(3'-pyrrolinium) chloride into 3$\alpha$-benziloyloxynortropane-8-spiro-1'-pyrrolidinium chloride 500 mg. 3$\alpha$-benziloyloxynortropane-8-spiro-1'-(3'-pyrrolinium) chloride are dissolved in 15 ml. methanol and, after the addition of a spatula tip of platinum dioxide, hydrogenated at normal pressure and at a temperature of 25° C. up to the end of the hydrogen takeup. The hydrogenation is carried out in a standard apparatus, such as is illustrated, for example, in Houben-Weyl, Methoden der organishen Chemie, 4th edition, Vol. IV/1c, pub. Georg Thieme Verlag, Stuttgart, New York, 1980, pp. 33-39. After filtering off the catalyst, the filtrate is evaporated to dryness in a vacuum. According to $^1$H-NMR spectroscopy, the reaction is quantitative. Crystallisation is carried out as described in Example 1, Step C.

EXAMPLE 3

3α-Benziloyloxynortropane-8-spiro-2'-isoindolinium chloride (1) 3α-Hydroxynortropane-8-spiro-2'-isoindolinium chloride 1.27 g. (10 mMole) nortropine are dissolved in 7 ml. chloroform and mixed with 1.46 g. (20 mMole) diethylamine and 4 g. (40 mMole) 1,2-bis-(chloromethyl)benzene. The clear solution is left to stand for 24 hours at ambient temperature in a closed vessel. It is then concentrated to one half and mixed with ethyl acetate in order to initiate crystallisation. The crystals are filtered off with suction and recrystallised from isopropanol/ethyl acetate. Yield 1 g. (38% of theory); m.p. 245°–247° C.

FD-MS: m/e=230 (molecule cation).

IR (KBr): $\gamma=3168, 757, 742$ cm$^{-1}$.

$^1$H-NMR (250 MHz, D$_2$O, δ-values referred to TSP=0): δ=2.09 (2H; H-6a, H-7a); 2.40–2.67 (4H; H-2, H-4); 2.59 (2H; H-6b, H-7b); 4.03 (2H; H-1, H-5); 4.24 (1H; H-3); 4.82 and 4.99 (4H; H-1' and H-3'); 7.47 (4H; H-4' to H-7').

(2) 3α-Benziloyloxynortropane-8-spiro-2'-isoindolinium chloride 1.33 g. (5 mMole) 3α-hydroxynortropane-8-spiro-1'-isoindolinium chloride is suspended in 210 ml. anhydrous acetonitrile and heated to 78° C. While stirring, there are first introduced 62 mg. (0.5 mMole) 4-dimethylaminopyridine and then, within the course of 2.5 hours, portionwise 3.2 g. (11.5 mMole) benzilic acid imidazolide. The reaction mixture is further stirred for 5.5 hours at 78° C., then cooled to 22° C. and further stirred overnight. The solution is concentrated to one quarter of its volume and the product caused to crystallise by the addition of ethyl acetate. Yield 1.3 g. (54% of theory); m.p. 263°–265° C.

FD-MS: m/e=440 (molecule cation).

IR (KBr): $\gamma=1740, 757, 703$ cm$^{-1}$.

$^1$H-NMR (250 MHz, D$_2$O, δ-values referred to TSP=0): δ=1.57 (2H; H-6a, H-7a); 2.03 (2H; H-2a, H-4a); 2.07 (2H; H-6b, H-7b); 2.70 (2H; H-2b, H-4b); 3.86 (2H; H-1, H-5); 4.69 amd 4.96 (4H; H-1'- and H-3'); 5.32 (1H; H-3); 7.40–7.51 (14H; H-4' to H-7' and aromatic protons of the benzilic acid).

EXAMPLE 4

3α-Benziloxyoxynortropane-8-spiro-4'-morpholinium chloride (1) 3α-Hydroxynortropane-8-spiro-4'-morpholinium chloride 11.8 ml. (113.2 mMole) diethylamine and 26.6 ml. (226.5 mMole) 2,2'-d-chlorodiethyl ether are stirred into a solution of 7.2 g. (56.6 mMole) nortropine and 70 ml. chloroform. The clear reaction solution is left to stand for 3 days at ambient temperature in a closed vessel. The oil-crystal mixture which separates out is homogenised and crystallised through overnight at 0° C. The crystals are filtered off with suction, washed with a little chloroform and dried under a vacuum at 40° C. for 2 hours. Additional substance is obtained by evaporating the mother liquor and treating with ethyl acetate. Yield 12.5 g. (95% of theory); m.p. 274°–276° C. (decomp.).

FD-MS: m/e=198 (molecule cation).

IR (KBr): $\gamma=3320, 892$ cm$^{-1}$.

$^1$N-NMR (250 MHz, D$_2$O, δ-values referred to TSP=0): δ=2.00 (2H; H-6a, H-7a); 2.22–2.62 (6H; H-2, H-4, H-6b, H-7b); 3.50 and 3.65 (4H; H-2' and H-6'); 4.01 and 4.08 (4H; H-2' and H-6'); 4.18 (1H; HO3); 4.22 (2H; H-1 and H-5).

(2) 3α-Benziloxyloxnortropane-8-spiro-4-morpholinium chloride 7.5 g. (32 mMole) 3α-hydroxynortropane-8-spiro-4'-morpholinium chloride are suspended in 650 ml. anhydrous acetonitrile and mixed with 0.587 g. (4.8 mMole) 4-(dimethylamino)-pyridine. 26 g. (92.8 mMole) benzilic acid imidazolide are added portionwise at 79° C. within the course of 3 hours. The reaction mixture is left to stand for 7 days at ambient temperature and the pure crystalline product is then filtered off with suction. The crystals obtained are dried under vacuum for 2 hours at 40° C.; yield 8.4 g. (60% of theory); m.p. 225° C. (decomp.).

FD-MS: m/e=408 (molecule cation).

IR (KBr): $\gamma=3410, 3183, 1731, 1492, 703$ cm$^{-1}$.

$^1$H-NMR (250 MHz, D$_2$O, δ-values referred to TSP=0): δ=1.51 (2H; H-6a, H-7a); 2.00 (4H; H-2a, H-4a, H-6b, H-7b); 2.63 (2H; H-2b, H-4b); 3.38 and 3.64 (4H; H-2' and H-6'); 3.99 and 4.04 (4H; H-3' and H-5'); 4.09 (2H; H-1, H-5); 5.30 (1H; H-3); 7.46 (10H; aromatic protons of the benzilic acid).

EXAMPLE 5

3α-Benziloxyoxynortropane-8-spiro-1'-pyrrolidino-[3',4'-b]quinoxalinium bromide (1) 3α-Hydroxynortropan-8-spiro-1'-pyrrolidino[3',4'-b]quinoxalinium bromide 4.58 g. (43.6 mMole) diethylamine and 13.85 g. (43.6 mMole) 2,3-bis-(bromoethyl)-quinoxaline are stirred into a solution of 5.57 g. (43.6 mMole) nortropine and 100 ml. chloroform. The reaction mixture, which has become warm, is cooled to 20° C., the product thereby precipitating out in crystalline form. It is filtered off with suction, washed with chloroform and dried in a vacuum for 22 hours at 55° C. Yield 11.1 g. (71% of theory); m.p. 283° C. (decomp.).

FD-MS: m/e=282 (molecule cation).

IR (KBr): $\gamma=3345, 1504, 773$ cm$^{-1}$.

$^1$H-NMR (250 MHz, D$_2$O, δ-values referred to TSP=0): δ=2.21; (2H; H-6a, H-7a); 2.53–2.89 (6H; H-2, H-4, H-6b, H-7b); 4.29 (2H; H-1 and H-5); 4.31 (1H; H-3); 5.21 and 5.41 (each 2H; H-2' and H-5'); 7.94–8.05 (2H; quinoxaline o-protons); 8.11–8.22 (2H; quinoxaline m-protons).

(2) 3α-Benziloyloxynortropane-8-spiro-1'-pyrrolidino[3',4'-b]quinoxalinium bromide 5 g. (1.39 mMole) 3α-hydroxynortropane-8-spiro-1'-pyrrolidino[3',4'-b]-quinoxalinium bromide are suspended in 130 ml. dried dimethyl sulphoxide and 100 ml. dry acetonitrile. After the addition of 0.26 g. (2.09 mMole) 4-dimethylaminopyridine, the reaction mixture is heated to 78° C. While stirring vigorously, 7.74 g. (27.8 mMole) benzilic acid imidazolide are added to 3 portions at intervals of 30 minutes. The reaction mixture is further stirred for 2.5 hours at 78° C. and is then cooled to 20° C. and filtered. The filter residue is discarded. The filtrate is evaporated to dryness at about 0.2 mbar pressure. The residue is extracted with 500 ml. boiling isopropanol and filtered hot. The filter residue is discarded. The filtrate is concentrated to 200 ml. The product crystallises out after standing overnight at ambient temperature. It is filtered off with suction, washed with cold isopropanol and dried in a vacuum for 2 hours at 55° C. Yield 3.5 g. (44% of theory); m.p. 205° C. (decomp.).

FD-MS: m/e=492 (molecule cation).

IR (KBr): γ=3375, 1730, 1504, 763 cm$^{-1}$.

$^1$H-NMR (250 MHz, CDCl$_3$/CD$_3$OD=3:1 v/v, δ-values referred to TMS=0): δ=1.78 (2H; H-6a, H-7a); 2.08 (2H; H-2a, H-4a); 2.20 (2H; H-6b, H-7b); 2.85 (2H; H-2b, H-4b); 4.23 (2H; H-1, H-5); 4.62 (4H; H-2', H-5'); 5.35 (1H; H-3); 7.30–7.48 (10H; benzilic acid protons); 7.84–7.97 (2H; quinoxaline o-protons); 8.07–8.22 (2H; quinoxaline m-protons).

EXAMPLE 6

3α-Benziloyloxynortropane-8-spiro-2'-(2'-aza-3H-phenolenium) bromide (1) 1.33 ml. (12.7 mMole) diethylamine and 4 g. (12.7 mMole) 1,8-bis-(bromoethyl)-naphthalene are stirred into a solution of 1.62 g. (12.7 mMole) nortropine and 75 ml. N,N-dimethylformamide. From the reaction mixture, which has become slightly warm, the product crystallises out within 2 hours. It is filtered off with suction, washed with a little N,N-diemthylformamide and dried in a vacuum at 55° C. for 2 hours. Yield 3.5 g. (76% of theory); m.p. 330° C. (decomp.).

FD-MS: m/e=280 (molecule cation):

IR (KBr): γ=3410, 1604, 1512 cm$^{-1}$.

$^1$H-NMR (250 MHz, CDCl$_3$/CD$_3$OD=3:1 v/v, δ-values referred to TMS=0): δ=2.02 (2H; H-6a, H-7a); 2.39–2.85 (6H; H-2, H-4, H-6b, H-7b); 3.92 (2H; H-1, H-5); 4.28 (1H; H-3); 5.01 and 5.16 (4H; H-1' and H-3'); 7.51–7.64 (4H; H-5', H-6', H-7', H-8'); 7.93 (2H; H-4', H-9').

(2)

3α-Benziloxyoxynortropane-8-spiro-2'-(2'-aza-3H-phenolenium)-bromide 2.95 g. (8.2 mMole) 3α-hydroxynortropane-8-spiro-2'-(2'-aza-3H-phenolenium) bromide are suspended in 1660 ml. dry acetonitrile and 160 ml. dry N,N-dimethylformamide. After the addition of 152 mg. (1.2 mMole) 4-dimethylaminopyridine, the reaction mixture is heated to 78° C. 4.56 g. (16.4 mMole) benzilic acid imidazolide are added in three portions with vigorous stirring at intervals of 30 minutes. The reaction mixture is then stirred for 2.5 hours at 78° C. and the reaction mixture thereafter evaporated to one half. The precipitated crude product is filtered off with suction at 20° C. and suspended in methanol. The material which is insoluble in methanol is filtered off and discarded. The filtrate is concentrated until the crystallisation of the product commences. After crystallisation overnight at ambient temperature, the product is filtered off with suction and dried in a vacuum for 2 hours at 55° C. Yield 2.1 g. (42% of theory); m.p. 322° C. (decomp.).

FD-MS: m/e 490 (molecule cation).

IR (KBr): γ=3428, 3240, 1738, 1603, 1497 cm$^{-1}$.

$^1$H-NMR (250 MHz, CDCl$_3$/CD$_3$OD=3:1 v/v, δ-values referred to TMS32 0): δ=1.75 (2H; H-6a, H-7a); 1.94 (2H; H-2a, H-4a); 2.20 (2H; H-6b, H-7b); 2.80 (2H; H-2b, H-4b); 3.85 (2H; H-1, H-5); 4.93 and 5.19 (each 2H; H-1' and H-3'); 5.45 (1H, H-3); 7.31–7.46 (10H; benzilic acid proton); 7.47–7.67 (4H; H-5', H-6', H-7', H-8'); 7.93 (2H; H.4', H-9').

EXAMPLE 7

3α-Benziloyloxynortropane-8-spiro-1'-(4'-methyl)-piperidinium chloride (1)

3α-Hydroxynortropane-8-spiro-1'-(4'-methyl)-piperidinium chloride 7.62 g. (0.06 mole) Nortropine are dissolved in 200 ml. anhydrous N,N-dimethylformamide. After stirring in 8.76 g. (0.12 mole) diethylamine and 37.18 g. (0.24 mole) 1,5-dichloro-3-methylpentane, the reaction mixture is left to stand for 18 days at ambient temperature in a closed vessel. The crystals which separate out are filtered off with suction, washed with a little dry acetonitrile and dried in a vacuum drying cabinet at 50° C. There are obtained 7.84 g. (53% of theory) of pure product; m.p. 290° C. (decomp.).

FD-MS: m/e=210 (molecule cation).

IR (KBr): γ=3190 cm$^{-1}$.

$^1$H-NMR (250 MHz, D$_2$O, δ-values in ppm, referred to TSP=0): δ=1.01 (m; 3H; CH$_3$); 1.37–2.02 (m; 7H; H-6a, H-7a, H-3', H-4', H-5'); 2.20–2.52 (m; 5H; H-2a, H-4a, H-6b, H-7b, OH); 2.60 and 2.67 (2×t; 2H; H-2b and H-4b); 3.10, 3.20, 3.63 and 3.74 (4×m; 4H; H-2' and H-6'); 3.76 and 4.24 (2×m; 2H; H-1 and H-5); 4.19 (t; 1H; H-3).

3α-benziloyloxynortropane-8-spiro-1'-(4'-methyl)-piperidinium chloride 7.37 g. (30 mMole) 3α-Hydroxynortropane-8-spiro-1'-(4'-methyl)-piperidinium chloride are suspended in 650 ml. anhydrous acetonitrile and heated to 78° C., while stirring. At this temperature, there are first stirred in 587 mg. (4.8 mMole) 4-(dimethylamino)pyridine and then, in the course of 2 hours, 13.35 g. (48 mMole) benzilic acid imidazolide in 4 approximately equal portions. Stirring is continued for 1.5 hours at 78° C. and then the reaction mixture is allowed to cool overnight at ambient temperature, without stirring. The crystalline product is filtered off with suction and washed with a little acetone. The crude crystallisate is recrystallised from dry isopropanol. The pure crystals are dried in a vacuum for 2 hours at 40° C. Yield 9.56 g. (70% of theory) as a 1:1 mixed crystallisate with isopropanol; m.p. 256°–259° C.

FD-MS: m/e=420 (molecule cation).

IR (KBr): γ=1735 cm$^{-1}$.

$^1$H-NMR (250 MHz, D$_2$O, δ-values in ppm, referred to TSP=0): δ=0.98 (m; 3H; CH$_3$); 1.30–1.65 (m; 4H; H-6a, H-7a, H-3'a, H-5'a); 1.65–2.03 (m; 7H; H-2a, H-4a, H-6b, H-7b, H-3'b, H-4', H-5'b); 2.52 and 2.72 (2H; H-2b, H-4b); 3.02, 3.19, 3.47, 3.72 (t, t; d; 4H; H-2' and H-6'); 3.62 and 4.10 (m, m; 2H; H-1 and H-5); 5.30 (t; 1H; H-3); 7.40–7.40 (m; 10H, aromatic protons).

EXAMPLE 8

3α-(4,4'-Difluorobenziloyloxy)-nortropane-8-spiro-1'-pyrrolidinium chloride 2.17 g. (0.01 mole) 3α-hydroxynortropane-8-spiro-1-pyrrolidinium chloride are dissolved with 2.02 g. (0.01 mole) sodium heptane-1-sulphonate, with warming, in 500 ml. anhydrous acetonitrile. After cooling to 25° to 27° C., the sodium chloride precipitate is filtered off with suction with the exclusion of moisture. The solution is mixed with 0.125 g. 4-(dimethylamino)pyridine and transferred to a reaction vessel which is connected to a stirrer vessel in which 4,4'-difluorobenzilic acid imidazolide is prepared. This stirrer vessel is equipped with two dropping funnels. In one dropping funnel, there are placed 2.64 g. (0.01 mole) 4,4'-difluorobenzilic acid (preparation analogous to the description in Federal Republic of Germany patent specification No. 20 34 943), dissolved in 100 ml. anhydrous acetonitrile. In the other dropping funnel there is placed a solution of 2.43 g. (0.015 mole) N,N-carbonyldiimidazole in 150 ml. anhydrous acetonitrile. From each of the two solutions, about one quarter of the volume is run in simultaneously, while stirring, into the stirrer vessel, the mixture is then stirred for 15 minutes and the resultant imidazolide solution transferred, with the strict exclusion of moisture, into the reaction vessel in which the solution of 3α-hydroxynortropane-8-spiro-1'-pyrrolidinium heptanesulphonate is stirred at ambient temperature. This procedure is repeated three times until all the reactants have been combined. The reaction mixture is then boiled under reflux for 2 hours and subsequently cooled overnight to ambient temperature. The reaction mixture is then evaporated to dryness in a rotary evaporator under vacuum. The residue is purified chromatographically over a silica gel column (silica gel 60, 0.063–0.200 mm., Merck No. 7734), the mobile phase being 1,2-dichloroethane:acetic acid:methanol: water 57:23:13:7 v/v/v/v). Yield 870 mg. (14% of theory) 3α-(4,4'-difluorobenziloyloxy)-nortropane-8-spiro-1'-pyrrolidinium heptanesulphonate. After passage over a column packed with a strongly basic ion exchanger in the chloride form (Lewatit MP 500), there is obtained the title compound. The crude product is recrystallised from isopropanol, washed with ethyl acetate and dried in a vacuum under vacuum at 40° C. to constant weight. Yield 470 mg. as 1:1 mixed crystallisate with isopropanol; m.p. 242°–245° C.

FD-MS: m/e=428 (molecule cation).

IR (KBr): $\gamma$=1508, 1603, 1733 cm$^{-1}$.

$^1$H-NMR (250 MHz, D$_2$O, δ-values in ppm, referred to TSP=0): δ=1.44–1.67 (m; 2H; H-6a, H-7a); 2.00–2.20 (m; 8H; H-2a, H-4a, H-6b, H-7b, H-3', H-4'); 2.57 and 2.64 (2×m; 2H; H-2b and H-4b); 3.38 and 3.60 (2×m; 4H; H-2', H-5'); 3.73 (m; 2H; H-1, H-5); 5.27 (t; 1H; H-3); 7.19 and 7.42 (2×m; 8H; aromatic protons).

EXAMPLE 9

3α-(4,4'-Dimethylbenziloyloxy)-nor tropane-8-spiro-1'-pyrrolidinium chloride

The procedure is as in Example 8 but instead of 4,4'-difluorobenzilic acid there is used 4,4'-dimethylbenzilic acid as starting material (preparation analogous to J. G. Cannon, J. Org. Chem., 25, 959–962/1960). Yield 1.68 g.; m.p. 175° C.

FD-MS: m/e=420 (molecule cation)

IR (KBr): $\gamma$=1508, 1612 (weak), 1718 cm$^{-1}$.

$^1$H-NMR (250 MHz, D$_2$O, δ-values in ppm, referred to TSP=0): δ=1.47–1.51 (m; 2H; H-6-a, H-7a); 1.79–2.21 (m; 8H; H-2a, H-4a, H-6b, H-7b, H-3', H-4'); 2.33 (s; 6H; 2×CH$_3$); 2.48–2.66 (m; 2H; H-2b, H-4b); 3.34 and 3.58 (2×m; 4H; H-2' and H-5'); 3.67 (m; 2H; H-1, H-5); 5.23 (t; 1H; H-3); 7.20–7.31 (m; 8H; aromatic protons).

EXAMPLE 10

3α-(4,4'-Di-n-butyloxybenziloyloxy)-nortropane-8-spiro-1'-pyrrolidinium chloride The procedure is as in Example 8 but instead of 4,4'-difluorobenzilic acid there is used 4,4-di-n-butyloxybenzilic acid as starting material (preparation analogous to J. G. Cannon, J. Org. Chem., 25, 959–962/1960). Yield 240 mg. of crystals which deliquesce at ambient temperature.

FD-MS: m/e/=536 (molecule cation).

IR (KBr): $\gamma$=1508, 1580 (weak), 1608, 1734 cm$^{-1}$.

$^1$H-NMR (250 MHz, CDCl$_3$, δ-values in ppm, referred to TSP=0): δ=0.96 (t; 6H; 2×CH$_3$ of n-butyloxy); 1.47 (t; q; 4H; 2×CH$_3$ of n-butyloxy); 1.53–1.63 (m; 2H; H-6a, H-7a); 1.76 (t, t; 4H; 2×CH$_3$ of n-butyloxy); 1.80–2.30 (m; 8H; H-2a, H-4a, H-6b, H-7b, H-3', H-4'); 2.62–2.77 (m; 2H; H-2b, H-4b); 3.65 and 3.99 (2×m; 4H; H-2' and H-5'); 3.94 (t; 4H; 2×CH$_3$ of n-butyloxy); 4.16 (m; 2H; H-1, H-5); 5.28 (t; 1H; H-3); 6.84 and 7.25 (2×d; 8H; aromatic protons).

EXAMPLE 11

3α-(4-n-butyloxybenziloyloxy)-nortropane-8-spiro-1'-pyrrolidinium chloride

The procedure is as in Example 8 but instead of 4,4'-difluorobenzilic acid there is used 4-n-butyloxybenzilic acid as starting material (preparation analogous to C. D. Shacklett and H. A. Smith, J.A.C.S., 75, 2654–2657/1953). Yield 250 mg.; m.p. 206° C.

FD-MS: m/e=464 (molecule cation).

IR (KBr): $\gamma$=1512, 1609, 1742 cm$^{-1}$.

$^1$H-NMR (250 MHz, CDCl$_3$, δ-values in ppm, referred to TMS=0): δ=0.97 (t; 3H; CH$_3$ of n-butyloxy); 1.50 (t, q; 2H; CH$_2$ of n-butyloxy); 1.56–1.64 (m; 2H; H-6a, H-7a); 1.77 (t,t; 2H; CH$_2$ of n-butyloxy); 1.84–2.45 (m; 8H; H-2a, H-4a, H-6b, H-7b, H-3', H-4'); 2.65–2.85 (m; 2H; H-2b, H-4b); 3.58 and 3.95 (2×m; 4H; H-2' and H-5'); 3.95 (t; 2H; CH$_2$ of n-butyloxy); 4.08 (m; 2H; H-1 and H-5); 5.30 (t; 1H; 6.84 (d) and 7.26–7.37 (m; 9H; aromatic protons).

GALENICAL EXAMPLES

1. Tablets 40 mg. azoniaspironortropanol ester according to one of the chemical Examples
20 mg. lactose
30 mg. starch
0.5 mg. magnesium stearate
74.5 mg. microcrystalline cellulose 2. Suppositories 120 mg. azoniaspironortropanol ester according to one of the chemical Examples
2 mg. "Aerosil" 200 (silicic acid)
2278 mg. Witepsol (modified triglycerides of saturated plant fatty acids)

3. Solution for Intravenous Injection 20 mg. azoniaspironortropanol ester according to one of the chemical Examples
4.6 mg. citric acid monohydrate
14.8 mg. sodium citrate dihydrate
ad 2 ml.

4. Solution for Intravenous Infusion 500 mg. azoniaspironortropanol ester according to one of the chemical Examples
130 mg. citric acid monohydrate
370 mg. sodium citrate dihydrate
ad 50 ml.

5. Retard Form: Diffusion Pellets

| Per hard gelatine capsule: | | | |
|---|---|---|---|
| | Without initial dose | | With initial dose |
| sugar spheroids | 150 mg. | | 150 mg. |
| azoniaspironortropanol ester according to one of the chemical Examples | 80 mg. | WS | 60 mg. |
| hydroxypropylcellulose (Klucel) | 10 mg. | | 8 mg. |
| acrylic or methacrylic esters: | | | |
| Endragit RL | 2 mg. | | 2 mg. |
| Endragit RS | 8 mg. | | 8 mg. |
| polyethyleneglycol (8000) | 1 mg. | | 1 mg. |
| talc | 5 mg. | | 5 mg. |
| | | WS | 20 mg. |
| | | Klucel | 2 mg. |

6. Retard Form: Matrix Tablet 80 mg. azoniaspironortropanol ester according to one of the chemical Examples
120 mg. lactose
15 mg. ethyl cellulose
20 mg. starch
2 mg. magnesium stearate
3 mg. polyethylene glycol (8000)

7. Retard Form: Two-Layer Tablet with Initial Dose

| | 1st layer retard tablet | 2nd layer retard tablet |
|---|---|---|
| azoniaspironortropanol ester | 60 mg. | 20 mg. |
| lactose | 90 mg. | 10 mg. |
| ethyl cellulose | 12 mg. | — |
| starch | 15 mg. | 15 mg. |
| magnesium stearate | 1.5 mg. | 0.3 mg. |
| polyethylene glycol (8000) | 2 mg. | — |
| microcrytalline cellulose | — | 37.2 mg. |

8. Dosed Aerosol for Inhalation

Formulation per dosage/spray impulse:
0.1 mg. azoniaspironortropanol ester according to one of the chemical Examples
0.02 mg. Span 85 (sorbitan mono- and trifatty acid residue based on oleic acid)
10 μl. Frigen 11 (trichlorofluoromethane)
40 μl. Frigen 12 (dichlorodifluoromethane).

9. Dosed Spray for Nasal use

Formulation per dosage/spray impulse:
2 mg. azoniaspironortropanol ester according to one of the chemical Examples
90 μl. physiological saline The following compounds according to the present invention have been tested for spasmolytic effectiveness:

3α-benziloyloxynortropane-8-spiro-1'-(3'-pyrrolinium) chloride (Example 2)
3α-benziloyloxynortropane-8-spiro-2'-isoindolinium chloride (Example 3)
3α-benziloyloxynortropane-8-spiro-4'-morpholinium chloride (Example 4)
3α-benziloyloxynortropane-8-spiro-1'-pyrrolidino[3',4'-b]quinoxalinium bromide (Example 5)
3α-benziloyloxynortropane-8-spiro-2'-(2'-aza-3H-phenolenium)bromide (Example 6).

As known comparison compound, there was used trospium chloride (Example 1).

The experiments were carried out on isolated rat intestine.

Animal material:

Male and female Wistar rats with a body weight of 150 to 250 g. The animals were acclimatised for 1 week at 20°±2° C. and at a relative humidity of 50+10%. The room illumination was daylight with additional neon tubes with a day/night illumination rhythm of 7.00 to 18.00 hours. The animals were kept in Makrolon cages type 4, each being occupied by 10 rats. The cages had a sawdust bedding. The feed was "ssniff" standard feed (Versuchstierdiäten GmbH, 4770 Soest, Germany) available ad libitum and the drinking water, which was tap water from synthetic resin flasks with stainless steel drinking tubes, was available ad libitum.

Substances, dosages:
test substances: compounds of Examples 1–6.
solvent: demineralised water
concentration: $1.185 \times 10^{-8}$ g./ml. bath vessel contents (against Carbachol)
volume administered: 0.25 ml.
time of action before administration of spasmodic: 3 minutes
further substances used: carbamoylcholine (Carbochol) hydrochloride, Merck, Darmstadt (Art No. 500 940)
sum formula: $C_6H_{15}ClN_2O_2$
concentrations:
$4 \times 10^{-9}$ g./ml. bath vessel content
$2 \times 10^{-8}$ g./ml. bath vessel content
$1 \times 10^{-7}$ g./ml. bath vessel content
$5 \times 10^{-7}$ g./ml. bath vessel content
$2.5 \times 10^{-6}$ g./ml.. bath vessel content
$1.25 \times 10^{-5}$ g./ml. bath vessel content
$6.25 \times 10^{-5}$ g./ml. bath vessel content
volume administered: 0.25 ml.
time of action: 5 minutes Ringer's nutrient solution with the following composition:

| | |
|---|---|
| sodium chloride = 9.000 g. | (E. Merck, Darmstadt) |
| potassium chloride = 0.210 g. | " |
| sodium bicarbonate = 0.500 g. | " |
| glucose monohydrate = 0.500 g. | " |
| calcium chloride monohydrate = 0.318 g. | " |

Carrying out of the Experiments

The rats were sacrificed by a neck blow. The abdomen was opened along the median line, an approximately 10 cm. long piece of ileum was removed, immediately transferred to a physiological tempered nutrient solution and then completely and carefully rinsed through twice in toto with the help of a 10 ml. syringe with nutrient solution for the removal of the intestinal contents. For the subsequent experiments, two pieces of intestine of 2 cm. length were separated off and the remaining piece of intestine kept in a refrigerator. The two pieces of intestine were freed in nutrient solution from tissue possibly still attached thereto. Around one end there was applied a sling of silk thread for fixing the piece of intestine in an organ bath, while around the other end was applied a longer thread with a connecting clamp for fixing to a recording layer. The piece of organ was thereafter filled with nutrient solution and suspended in a bath vessel with Carbogen bubbling therethrough and loaded with 0.5 g. After a resting period of 30 minutes, the experiment can commence.

There was first plotted a dosage action relationship of the spasmodic. The solution to be tested was injected by means of a tuberculin syringe with applied single-use canule into the bath liquid. Depending upon the volume to be injected, for the precise maintenance of the bath content there was previously always removed an equal volume of nutrient solution. Concentrations were selected which, in geometric steps of a factor of 5, displayed spasmodic effects of >10% to 100%, the 100% effect being taken as being the limiting concentration, exceeding of which brought about no greater effect. The limiting concentration is taken as reference value and the effects of the lower concentrations were calculated to refer to this 100% value. A complete concentration activity curve was plotted using a piece of intestine.

The period of action of the spasmodic on the organ was 5 minutes. Thereafter, the content of the bath vessel was changed three times by rinsing and followed by a resting phase (no addition of substance) of 30 minutes.

After plotting of the concentration-activity relationship of the spasmodic, the antagonistic strength of action of the substance to be tested was tested. For this purpose, the test substance was injected in a constant concentration into the bath vessel content 3 minutes before application of the spasmodic. The subsequent course of the experiment corresponded to that already described: addition of spasmodic in increasing concentrations, rinsing three times, 30 minute resting phase. Depending upon the effect, the concentrations of the test substance were varied, ten experiments being carried out per concentration.

Analysis and Apparatus

The experimental apparatus consisted of a horizontally fixed, about 66 cm. long cylinder-shaped glass surround with inlet and outlet taps in which were melt-sealed two pre-heating spirals which were provided on the outside with inlet pipes and each of which open downwardly into a bath vessel of 25 ml. volume closable below by stopcocks. Demineralised water warmed to 34° C. was circulated by an ultrathermostat of the firm "Colora" through the glass surround so that the nutrient solution present in the pre-heating spirals and bath vessels was always uniformly warmed. In case of need, it was passed from a higher-standing supply vessel via a tube system into the pre-heating spirals. On the bottom of the bath vessel, for the continuous bubbling through the nutrient solution with Carbogen (95% oxygen and 5% carbon dioxide), there were provided gassing tubes, on the limbs of which, in the lower third thereof, were melt-sealed glass hooks on to which were suspended on one end the previously prepared piece of intestine, whereas the other end was attached with its long thread with a metal recorder lever for MP recordal. Finally, the loading was adjusted on the recorder lever and the star recorder of the lever applied to the MP paper on the recorder drum (diameter 200 mm.) of a kymograph. During the experiment, the MP paper was rolled from the table unrolling device on to the drum. The paper movement was $2.62$ mm.$\times$min$^{-1}$. The recording breadth could be regulated via an MP generator with incorporated potentiometer. For a better current flow, a contact roller was additionally applied to the MP paper which was connected with the earthing box of the MP generator.

After ending of the experiment, the recordings on the MP paper were fixed with a special fixing spray.

All apparatus necessary for the recordings were obtained from the firm Braun, Melsungen, Germany.

Evaluation

For each concentration in g./ml. there was obtained the arithmetic average values and their standard deviations ($\underline{x}\% \pm s$) of the spasmodic effect.

Results

A 50% spasm was obtained with Carbachol alone (blank experiment) at a concentration of $4.3 \times 10^{-8}$ g./ml.

In the case of the use of the above-mentioned spasmolytically-acting test substances in a concentration of $1.18 \times 10^{-8}$ g./ml., for the initiation of a 50% spasm, carbachol concentrations of the order of $10^{-6}$ g./ml. were needed.

We claim:

1. Process for preparation of an azoniaspironortropanol ester, comprising reacting tropine with a $C_1$-$C_3$ chloroalkane containing at least one trichloromethyl group in the presence of an oxidizing agent under conditions favoring formation of nortropine, reacting said nortropine with a dihalide under conditions favoring formation of an azonia compound, said reaction taking place in the presence of an amine, and esterfying said azonia compound with an imidazolide in the presence of a catalyst under conditions favoring formation of an azoniaspironotropanol ester.

2. Process for preparation of an azoniaspironortropanol ester, comprising reacting tropine with a chloroformic acid ester in the presence of an acid binding agent under conditions favoring formation of an 8-alkoxycarbonylnortropine, hydrolyzing said 8-alkoxycarbonylnortropine in the presence of a base to form nortropine, alkylating said nortropine with a dihalide, alkylyzation taking place in the presence of an amine to form an azoniaspiro compound, and esterfying said azoniaspiro compound with an acid imidazolide in the presence of a catalyst to form said azoniaspironortropanol ester.

3. Process of claim 1, wherein said chloroalkane is selected from the group consisting of 1,1,1-trichloroethane, 1,1,1-trichloropropane, and chloroform.

4. Process of claim 1, wherein said chloroalkane is chloroform.

5. Process of claim 1, wherein said chloroalkane is used in an amount from 1% to 10% of the volume of said tropine.

6. Process of claim 5, wherein said chloroalkane is used in an amount from 1% to 5% of said tropine.

7. Process of claim 5, wherein said chloroalkane is used in an amount from 2% to 4% of said tropine.

8. Process of claim 1, wherein said oxidation agent is potassium ferricyanide.

9. Process of claim 2, wherein said tropine is reacted with a 4 to 6 fold excess of said chloroformic acid ester.

10. Process of claim 2, wherein said chloroformic acid ester is ethyl chloroformate.

11. Process of claim 2, wherein said acid-binding agent is an alkali metal carbonate or an alkali metal bicarbonate.

12. Process of claim 1 or 2, wherein said amine is a secondary or tertiary amine.

13. Process of claim 1 or 2, wherein said nortropine, amine, and dihalide are in a 1:2:4 molar ratio.

14. Process of claim 1 or 2, wherein said amine is a secondary amine selected from the group consisting of dimethylamine, diethylamine, diisopropylamine, and dicyclohexylamine.

15. Process of claim 1 or 2, wherein said amine is a tertiary amine selected from the group consisting of trimethylamine, triethylamine, pyridine, and quinoline.

16. Process of claim 1 or 2, wherein said catalyst is 4-(Dimethylamino)-pyridine.

* * * * *